United States Patent
LeClair et al.

(10) Patent No.: US 10,533,057 B2
(45) Date of Patent: *Jan. 14, 2020

(54) TREATMENT FOR MULTIPLE MYELOMA (MM)

(71) Applicant: MORPHOSYS AG, Planegg (DE)

(72) Inventors: Stéphane LeClair, Gauting (DE); Jan Endell, Munich (DE); Stefan Härtle, Jesenwang (DE)

(73) Assignee: MORPHOSYS AG, Planegg (DE)

( * ) Notice: Subject to any disclaimer, the term of this patent is extended or adjusted under 35 U.S.C. 154(b) by 106 days.

This patent is subject to a terminal disclaimer.

(21) Appl. No.: 15/569,495

(22) PCT Filed: May 13, 2016

(86) PCT No.: PCT/EP2016/060810
§ 371 (c)(1),
(2) Date: Oct. 26, 2017

(87) PCT Pub. No.: WO2016/180958
PCT Pub. Date: Nov. 17, 2016

(65) Prior Publication Data
US 2019/0048091 A1    Feb. 14, 2019

(30) Foreign Application Priority Data
May 13, 2015  (EP) .................................... 15167597

(51) Int. Cl.
| | | |
|---|---|---|
| *A61K 39/395* | (2006.01) | |
| *C07K 16/28* | (2006.01) | |
| *A61P 35/00* | (2006.01) | |
| *A61K 9/00* | (2006.01) | |
| *A61K 31/573* | (2006.01) | |

(52) U.S. Cl.
CPC ........ *C07K 16/2896* (2013.01); *A61K 9/0021* (2013.01); *A61K 31/573* (2013.01); *A61P 35/00* (2018.01); *A61K 2300/00* (2013.01)

(58) Field of Classification Search
CPC .................................................. C07K 16/2896
See application file for complete search history.

(56) References Cited

U.S. PATENT DOCUMENTS

| | | | | |
|---|---|---|---|---|
| 7,829,673 | B2 | 11/2010 | De Weers et al. | 530/387.1 |
| 8,088,896 | B2 | 1/2012 | Tesar | 530/387.1 |
| 8,153,765 | B2 | 4/2012 | Park et al. | 530/387.3 |
| 8,263,746 | B2 | 9/2012 | Tesar | 530/387.9 |
| 2002/0164788 | A1 | 11/2002 | Ellis | 435/328 |
| 2008/0152646 | A1* | 6/2008 | Anderson | A61K 31/454 424/133.1 |
| 2009/0123950 | A1 | 5/2009 | Tesar | 435/7.23 |
| 2010/0092489 | A1* | 4/2010 | Van De Winkel | A61K 39/39558 424/172.1 |

FOREIGN PATENT DOCUMENTS

| | | | | |
|---|---|---|---|---|
| WO | 1999/062526 | 12/1999 | | |
| WO | 2002/006347 | 1/2002 | | |
| WO | 2005/103083 | 11/2005 | | |
| WO | 2006/099875 | 9/2006 | | |
| WO | 2006/125640 | 11/2006 | | |
| WO | 2007/042309 | 4/2007 | | |
| WO | 2008/047242 | 4/2008 | | |
| WO | WO-2011154453 A1 * | 12/2011 | ......... C07K 16/2896 | |
| WO | 2012/041800 | 4/2012 | | |
| WO | WO-2014089279 A1 * | 6/2014 | ........... G01N 33/573 | |
| WO | WO 2015/195476 | 12/2015 | | |
| WO | WO-2016022589 A2 * | 2/2016 | ....... A61K 39/39558 | |
| WO | WO 2016/040294 | 3/2016 | | |

OTHER PUBLICATIONS

Office communication in EP 16 723 349.3-1111 dated Jan. 14, 2019.
ClinicalTrials.gov Archive "A Phase I/IIa Study of Human Anti-CD38 Antibody MOR03087 (MOR202) in Relapsed/Refractory Multiple Myeloma" U.S. National Library of Medicine, Mar. 2018.
Bauer, M. K. "CD38: A Unique Target in Multiple Myeloma" 1$^{st}$ Annual Summit of Practical and Emerging Trends in Multiple Myeloma, Mar. 2014.
International Search Report and Written Opinion in PCT/EP2016/060810 dated Jul. 15, 2016.

* cited by examiner

*Primary Examiner* — Sheela J. Huff
(74) *Attorney, Agent, or Firm* — Licata & Tyrrell P.C.

(57) ABSTRACT

The present disclosure relates to the treatment of multiple myeloma. Monoclonal antibody MOR202 is efficacious when administered to patient at certain dosage regimens.

5 Claims, 11 Drawing Sheets

Specification includes a Sequence Listing.

FIGURE 1

The amino acid sequence of the MOR202 Variable Heavy Domain is:

QVQLVESGGGLVQPGGSLRLSCAASGFTFSSYYMNWVRQAPGKGLEWVSGISGD
PSNTYYADSVKGRFTISRDNSKNTLYLQMNSLRAEDTAVYYCARDLPLVYTGFAYWGQGTL
VTVSS (SEQ ID NO: 8)

The amino acid sequence of the MOR202 Variable Light Domain is:

DIELTQPPSVSVAPGQTARISCSGDNLRHYYVYWYQQKPGQAPVLVIYGDSKRPSGI
PERFSGSNSGNTATLTISGTQAEDEADYYCQTYTGGASLVFGGGTKLTVLGQ (SEQ ID NO: 9)

The amino acid sequence of the MOR202 HCDR1 as defined by an internal nomenclature is: GFTFSSYYMN (SEQ ID NO: 1)

The amino acid sequence of the MOR202 HCDR1 as defined by Kabat is: SYYMN (SEQ ID NO: 2)

The amino acid sequence of the MOR202 HCDR2 as defined by Kabat is: GISGDPSNTYYADSVKG (SEQ ID NO: 3)

The amino acid sequence of the MOR202 HCDR3 as defined by Kabat is: DLPLVYTGFAY (SEQ ID NO: 4)

The amino acid sequence of the MOR202 LCDR1 as defined by Kabat is: SGDNLRHYYVY (SEQ ID NO: 5)

The amino acid sequence of the MOR202 LCDR2 as defined by Kabat is: GDSKRPS (SEQ ID NO: 6)

The amino acid sequence of the MOR202 LCDR3 as defined by Kabat is: QTYTGGASL (SEQ ID NO: 7)

* Best response > SD
** Trough levels below limit of quantification were displayed with half limit of quantification Infusion-related reactions

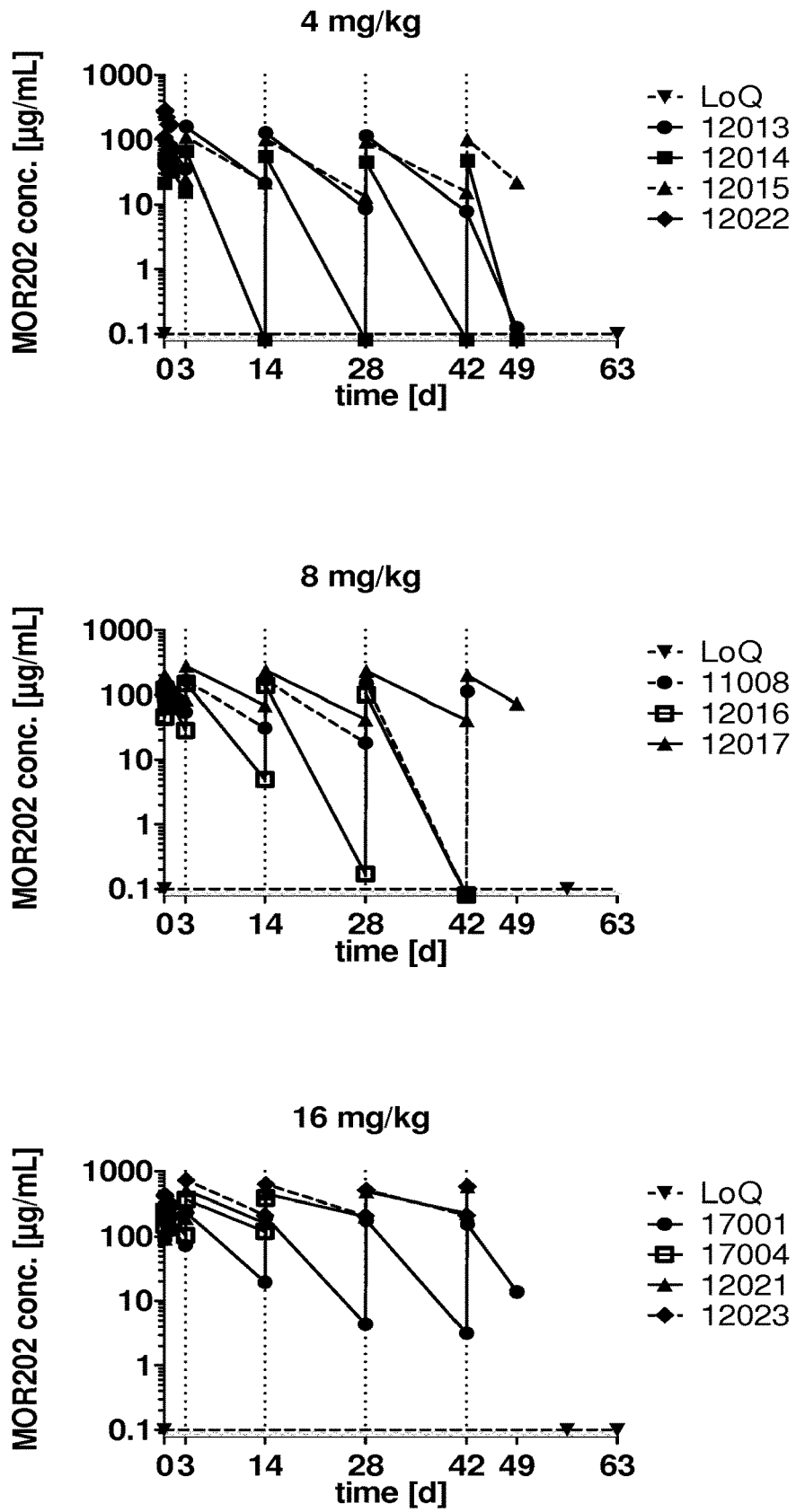
Figure 7A MOR202 serum concentrations for patients dosed at q2W for two cycles

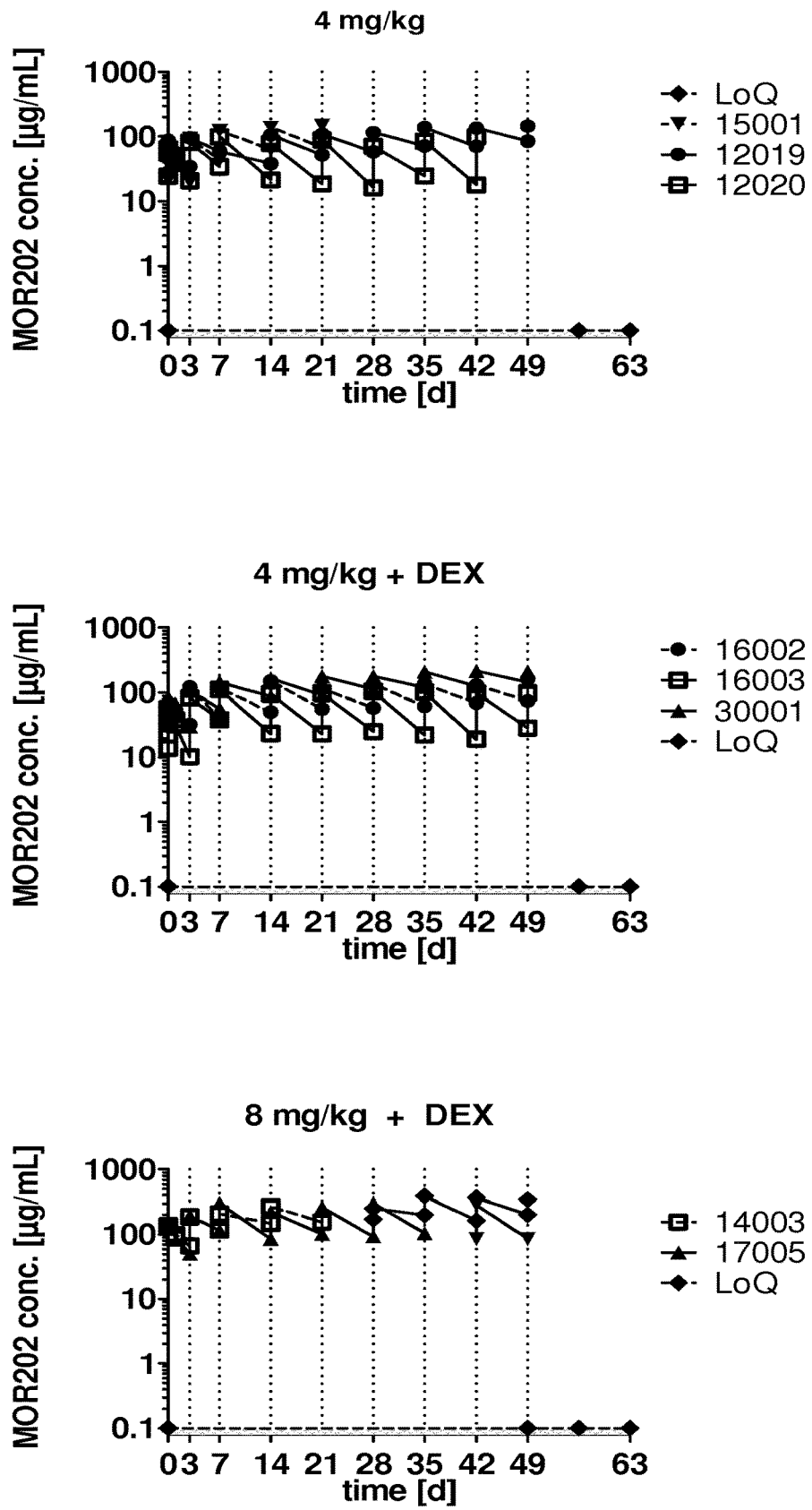
Figure 7B MOR202 serum concentrations for patients dosed at q1W for two cycles

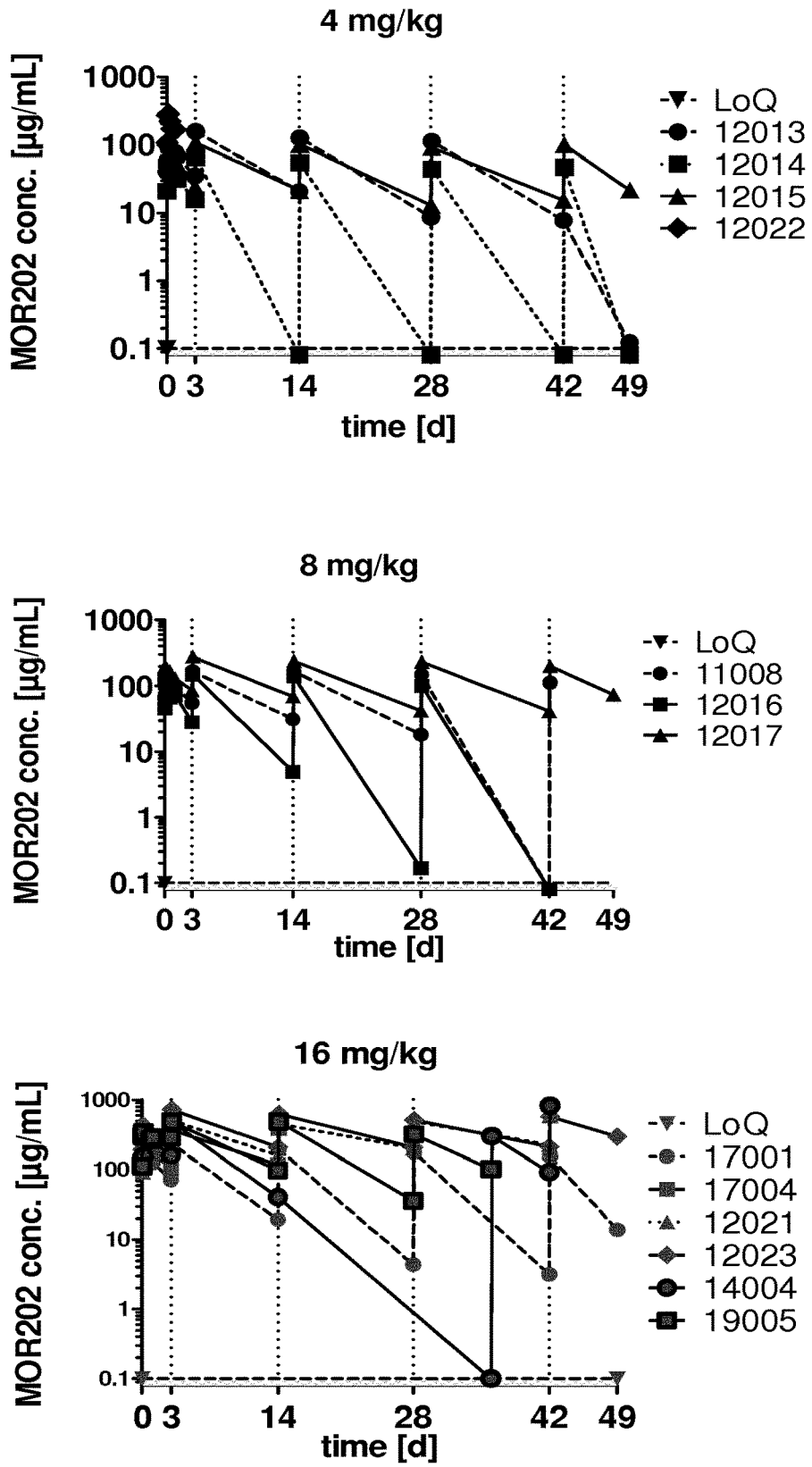
Figure 7C MOR202 serum concentrations for patients dosed at q2W for two cycles

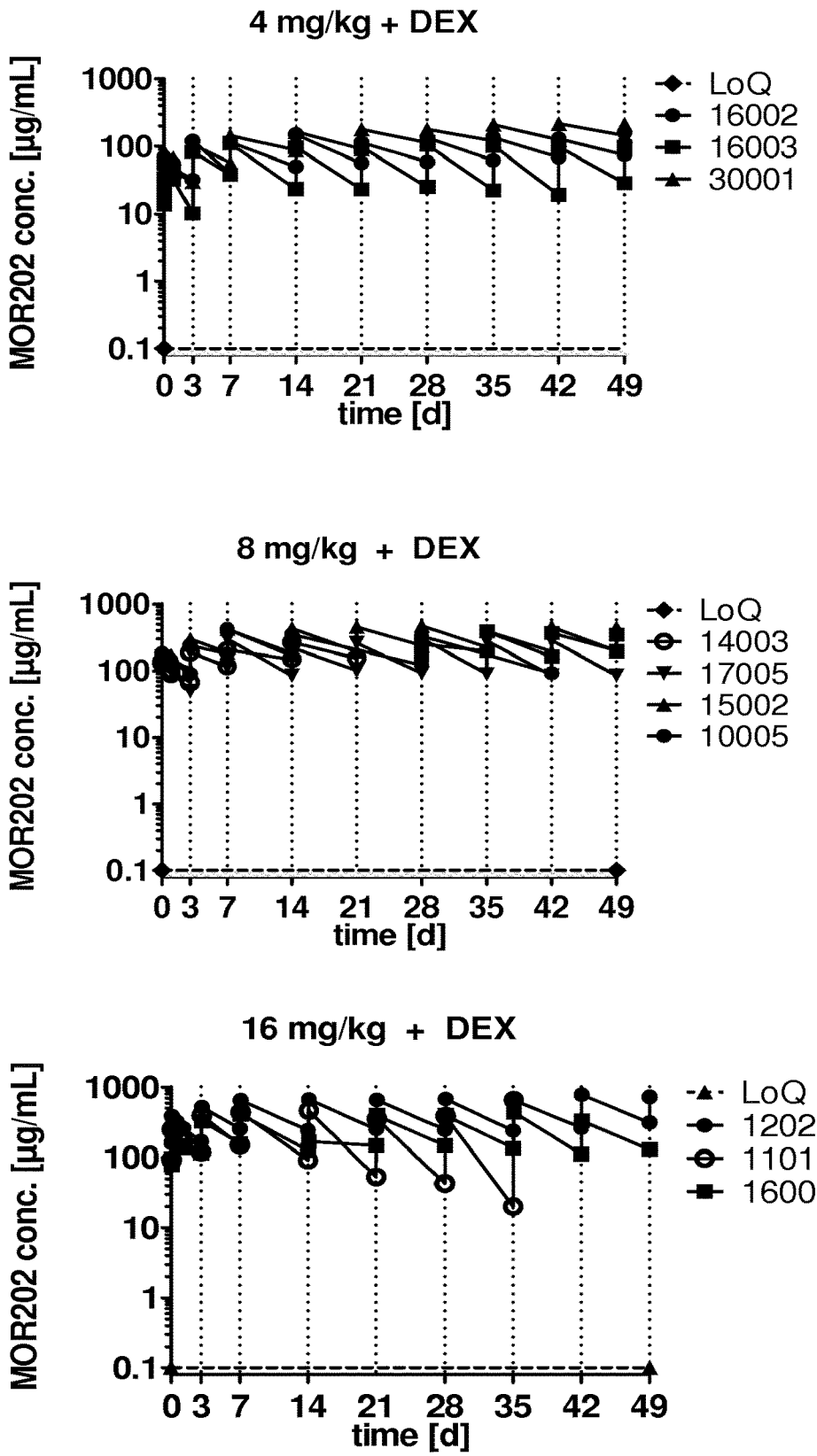
Figure 7D MOR202 serum concentrations for patients dosed at q1W for two cycles

TREATMENT FOR MULTIPLE MYELOMA (MM)

This patent application is the U.S. National Stage of International Application No. PCT/EP2016/060810 filed May 13, 2016, which claims the benefit of EP 15167597.2 filed May 13, 2015, each of which is incorporated by reference in its entirety.

SEQUENCE LISTING

The instant application contains a Sequence Listing which has been submitted electronically in ASCII format and is hereby incorporated by reference in its entirety. Said ASCII copy, created on May 4, 2016, is named MS231PCT_SL.txt and is 8,236 bytes in size.

BACKGROUND OF THE INVENTION

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). The incidence of MM increases in the aging population, with the median age at time of diagnosis being about 61 years. The currently available therapies for multiple myeloma include chemotherapy, stem cell transplantation, Thalomid® (thalidomide), Velcade® (bortezomib), Aredia® (pamidronate), and Zometa® (zoledronic acid). The current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, MM patients often relapse, even under maintenance therapy with interferon-alpha (IFN-α) alone or in combination with steroids.

CD38 is an example of an antigen expressed on such malignant B cells, plasma cells, and other lymphocytes. Functions ascribed to CD38 include both receptor mediation in adhesion and signaling events and (ecto-) enzymatic activity. As an ectoenzyme, CD38 uses NAD+ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for Ca2+ mobilization. By converting NAD+ to cADPR, CD38 regulates the extracellular NAD+ concentration and hence cell survival by modulation of NAD-induced cell death (NCID). In addition to signaling via Ca2+, CD38 signaling occurs via cross-talk with antigen-receptor complexes on T and B cells or other types of receptor complexes, e.g. MHC molecules, and is in this way involved in several cellular responses, but also in switching and secretion of IgG.

Antibodies specific for CD38 are described in WO1999/62526 (Mayo Foundation); WO200206347 (Crucell Holland); US2002164788 (Jonathan Ellis) which is incorporated by reference in its entirety; WO2005/103083 (MorphoSys AG), U.S. Ser. No. 10/588,568, which is incorporated by reference in its entirety, WO2006/125640 (MorphoSys AG), U.S. Ser. No. 11/920,830, which is incorporated by reference in its entirety, and WO2007/042309 (MorphoSys AG), U.S. Ser. No. 12/089,806, which is incorporated by reference in its entirety; WO2006099875 (Genmab), U.S. Ser. No. 11/886,932, which is incorporated by reference in its entirety; and WO08/047242 (Sanofi-Aventis), U.S. Ser. No. 12/441,466, which is incorporated by reference in its entirety.

SUMMARY

The present invention relates to certain surprising findings observed in the first in human clinical trial with the CD38 monoclonal antibody MOR202 in patients with relapsed or refractory Multiple Myeloma (MM).

In order to identify an appropriate dose for further study and treatment of patients, a thorough evaluation of the pharmacokinetic data and clinical responses was completed. Surprisingly a correlation was observed between overall response rate, duration of response, time to progression (TTP) and/or progression-free survival (PFS) of patients and a dosing of 8 mg/kg or more or 16 mg/kg or more.

Surprisingly it was found that the overall response rate of patients receiving administration of 16 mg/kg once weekly q1w was significantly improved over patients receiving 4 mg/kg once every other week q2w or 4 mg/kg once weekly q1w, and/or receiving 8 mg/kg once every other week q2w or 8 mg/kg once weekly q1w.

Accordingly, appropriate dose selection for further study and treatment of patients can be selected based upon such findings.

FIGURE LEGENDS

FIG. 1 shows the amino acid sequence of the variable domains of antibody MOR202.

FIGS. 7A-D show MOR202 serum concentrations over time in the clinical trial of MOR03087 (MOR202) in adult subjects with relapsed/refractory multiple myeloma.

Figure 8:
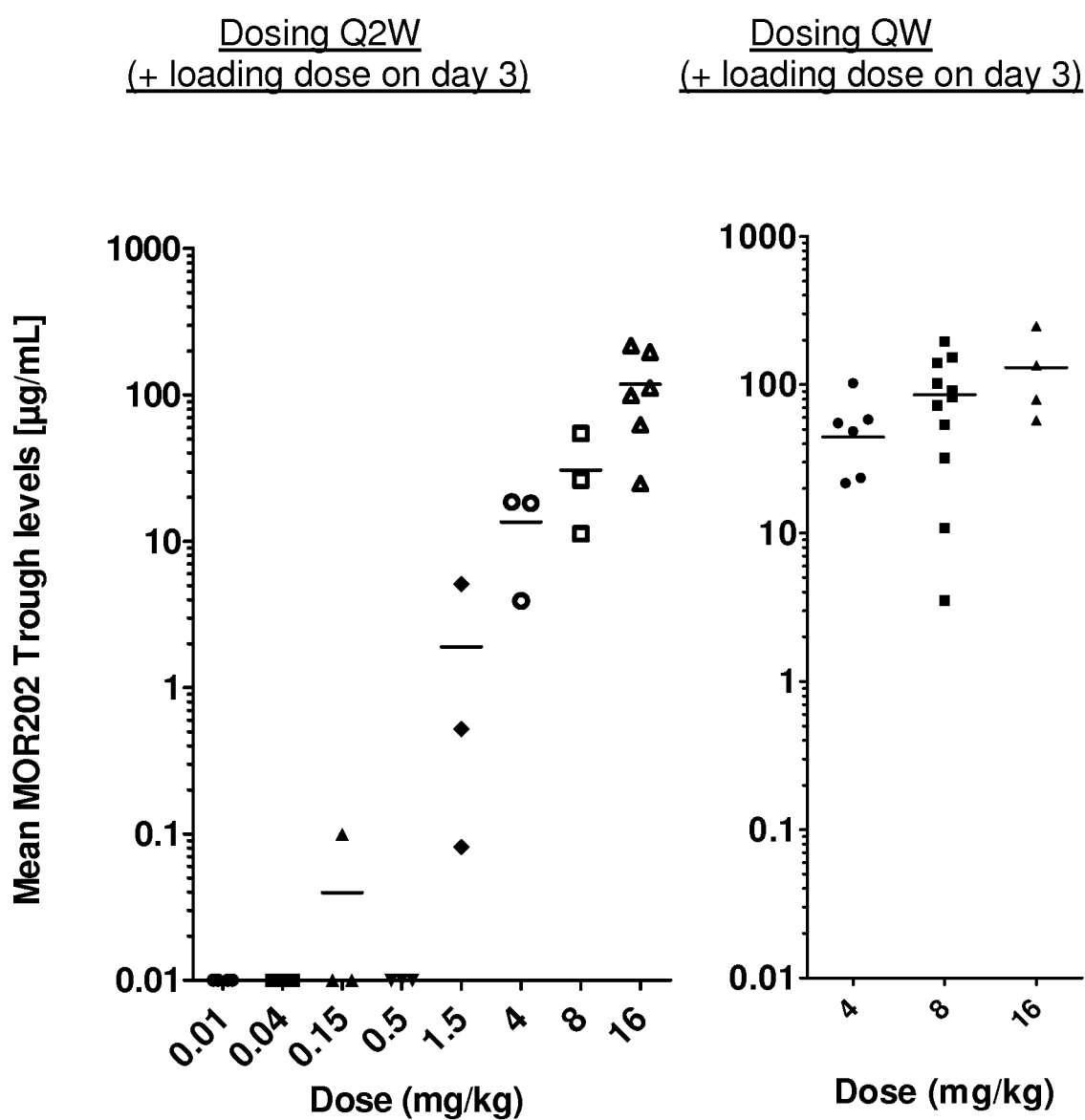

FIG. 8 shows the mean trough levels of MOR202 resulting from certain dosing regimens in the clinical trial of MOR03087 (MOR202) in adult subjects with relapsed/refractory multiple myeloma.

DETAILED DESCRIPTION OF THE INVENTION

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

"VH" refers to the variable region of an immunoglobulin heavy chain of an antibody, or antibody fragment. "VL" refers to the variable region of the immunoglobulin light chain of an antibody, or antibody fragment.

The "CDRs" herein are defined by either Chothia et al or Kabat et al. See Chothia C, Lesk AM. (1987) Canonical structures for the hypervariable regions of immunoglobulins. J Mol Biol., 196(4):901-17, which is incorporated by reference in its entirety. See Kabat E. A, Wu T. T., Perry H. M., Gottesman K. S. and Foeller C. (1991). Sequences of Proteins of Immunological Interest. 5th edit., NIH Publication no. 91-3242, US Dept. of Health and Human Services, Washington, D.C.

The term "CD38" refers to the protein known as CD38, having the following synonyms: ADP-ribosyl cyclase 1, cADPr hydrolase 1, Cyclic ADP-ribose hydrolase 1, T10.

Human CD38 has the amino acid sequence of:

```
                                         (SEQ ID NO: 10)
    MANCEFSPVSGDKPCCRLSRRAQLCLGVSILVLILVVVLAVVVPR

WRQQWSGPGTTKRFPETVLARCVKYTEIHPEMRHVDCQSVWDAFKGAFIS

KHPCNITEEDYQPLMKLGTQTVPCNKILLWSRIKDLAHQFTQVQRDMFTL

EDTLLGYLADDLTWCGEFNTSKINYQSCPDWRKDCSNNPVSVFWKTVSRR

FAEAACDVVHVMLNGSRSKIFDKNSTFGSVEVHNLQPEKVQTLEAWVIHG

GREDSRDLCQDPTIKELESIISKRNIQFSCKNIYRPDKFLQCVKNPEDSS

CTSEI.
```

"MOR202" an anti-CD38 antibody whose amino acid sequence is provided in FIG. 1. MOR202 is disclosed in U.S. Pat. No. 8,088,896, which is incorporated by reference in its entirety. "MOR202" and "MOR03087" are used as synonyms to describe the antibody shown in FIG. 1.

The DNA sequence encoding the MOR202 Variable Heavy Domain is:

```
                                         (SEQ ID NO: 11)
    CAGGTGCAATTGGTGGAAAGCGGCGGCGGCCTGGTGCAACCGGGC

GGCAGCCTGCGTCTGAGCTGCGCGGCCTCCGGATTTACCTTTTCTTCTTA

TTATATGAATTGGGTGCGCCAAGCCCCTGGGAAGGGTCTCGAGTGGGTGA

GCGGTATCTCTGGTGATCCTAGCAATACCTATTATGCGGATAGCGTGAAA

GGCCGTTTTACCATTTCACGTGATAATTCGAAAAACACCCTGTATCTGCA

AATGAACAGCCTGCGTGCGGAAGATACGGCCGTGTATTATTGCGCGCGTG
```

ATCTTCCTCTTGTTTATACTGGTTTTGCTTATTGGGGCCAAGGCACCCTG

GTGACGGTTAGCTCA.

The DNA sequence encoding the MOR202 Variable Light Domain is:

```
                                         (SEQ ID NO: 12)
    GATATCGAACTGACCCAGCCGCCTTCAGTGAGCGTTGCACCAGGT

CAGACCGCGCGTATCTCGTGTAGCGGCGATAATCTTCGTCATTATTATGT

TTATTGGTACCAGCAGAAACCCGGGCAGGCGCCAGTTCTTGTGATTTATG

GTGATTCTAAGCGTCCCTCAGGCATCCCGGAACGCTTTAGCGGATCCAAC

AGCGGCAACACCGCGACCCTGACCATTAGCGGCACTCAGGCGGAAGACGA

AGCGGATTATTATTGCCAGACTTATACTGGTGGTGCTTCTCTTGTGTTTG

GCGGCGGCACGAAGTTAACCGTTCTTGGCCAG.
```

MOR202 has an IgG1 Fc region.

A pharmaceutical composition includes an active agent, e.g. an antibody for therapeutic use in humans. A pharmaceutical composition may additionally include pharmaceutically acceptable carriers or excipients.

"Multiple myeloma" is also known as plasma cell myeloma, myelomatosis, or Kahler's disease (after Otto Kahler), and is a cancer of plasma cells, a type of white blood cell normally responsible for producing antibodies. In multiple myeloma, collections of abnormal plasma cells accumulate in the bone marrow, where they interfere with the production of normal blood cells. Most cases of multiple myeloma also feature the production of a paraprotein an abnormal antibody which can cause kidney problems. Bone lesions and hypercalcemia (high blood calcium levels) are also often encountered.

Multiple myeloma is diagnosed with blood tests (serum protein electrophoresis, serum free kappa/lambda light chain assay), bone marrow examination, urine protein electrophoresis, and X-rays of commonly involved bones.

M protein or myeloma protein is an abnormal immunoglobulin fragment or immunoglobulin light chain that is produced in excess by an abnormal clonal proliferation of plasma cells, typically in multiple myeloma.

"Administered" or "administration" refers to the delivery of a pharmaceutical composition by an injectable form, such as, for example, an intravenous, intramuscular, intradermal or subcutaneous route or mucosal route, for example, as a nasal spray or aerosol for inhalation or as an ingestable solution, capsule or tablet.

The antibody which is administered according to the present disclosure is administered to the patient in a therapeutically effective amount. A "therapeutically effective amount" refers to an amount sufficient to cure, alleviate or partially arrest the clinical manifestations of a given disease or disorder, i.e. MM, and its complications.

Mg/kg means milligram antibody per kilogram body weight.

"Cmax" refers to the highest plasma concentration of the antibody observed within the sampling interval.

"AUC" or "area under the curve" refers to the area under the plasma concentration-time curve, as calculated by the trapezoidal rule over the complete sample collection interval.

The drug dose that leads to a therapeutically effect can also be described in terms of the total exposure to a patient measured by area under the curve.

The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

The antibody of the present disclosure can be administered at different time points and the treatment cycle may have a different length. The antibodies may be administered daily, every other day, three times a week, weekly or biweekly. The antibodies may also be administered over at least four weeks, over at least five weeks, over at least six weeks, over at least seven weeks, over at least eight weeks, over at least nine weeks, over at least ten weeks, over at least eleven weeks or over at least twelve weeks.

The term "epitope" includes any protein determinant capable of specific binding to an antibody or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." The term "linear epitope" refers to an epitope with all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformation. In a conformational epitope, the points of interaction occur across amino acid residues on the protein that are separated from one another.

EMBODIMENTS

An aspect includes a method of treating multiple myeloma in a subject in need thereof comprising administering to the subject a therapeutically effective amount of an antibody specific for CD38 wherein said antibody comprises an HCDR1 region of sequence GFTFSSYYMN (SEQ ID NO: 1) or SYYMN (SEQ ID NO: 2), an HCDR2 region of sequence GISGDPSNTYYADSVKG (SEQ ID NO: 3), an HCDR3 of sequence DLPLVYTGFAY (SEQ ID NO: 4), an LCDR1 region of sequence SGDNLRHYYVY (SEQ ID NO: 5), an LCDR2 region of sequence GDSKRPS (SEQ ID NO: 6), and an LCDR3 region of sequence QTYTGGASL (SEQ ID NO: 7), wherein said antibody is administered at a dose of 8 mg/kg or more.

An aspect includes a use of an antibody specific for CD38 wherein said antibody comprises an HCDR1 region of sequence GFTFSSYYMN (SEQ ID NO: 1) or SYYMN (SEQ ID NO: 2), an HCDR2 region of sequence GISGDPSNTYYADSVKG (SEQ ID NO: 3), an HCDR3 of sequence DLPLVYTGFAY (SEQ ID NO: 4), an LCDR1 region of sequence SGDNLRHYYVY (SEQ ID NO: 5), an LCDR2 region of sequence GDSKRPS (SEQ ID NO: 6), and an LCDR3 region of sequence QTYTGGASL (SEQ ID NO: 7) in the manufacture of a medicament for the treatment of multiple myeloma, wherein said antibody is administered at a dose of 8 mg/kg or more.

In certain embodiments the present disclosure relates to an antibody specific for CD38 wherein said antibody comprises an HCDR1 region of sequence GFTFSSYYMN (SEQ ID NO: 1) or SYYMN (SEQ ID NO: 2), an HCDR2 region of sequence GISGDPSNTYYADSVKG (SEQ ID NO: 3), an HCDR3 of sequence DLPLVYTGFAY (SEQ ID NO: 4), an LCDR1 region of sequence SGDNLRHYYVY (SEQ ID NO: 5), an LCDR2 region of sequence GDSKRPS (SEQ ID NO: 6), and an LCDR3 region of sequence QTYTGGASL (SEQ ID NO: 7) for use in the treatment of multiple myeloma, wherein said antibody is administered at a dose of 8 mg/kg or more.

In an embodiment, the antibody comprises the HCDR1 region of sequence GFTFSSYYMN (SEQ ID NO: 1).

In an embodiment, the antibody comprises the HCDR1 region of sequence SYYMN (SEQ ID NO: 2).

In an embodiment, the multiple myeloma is relapsed/refractory.

In certain embodiments, the disclosed antibody specific for CD38 is administered at a dose of 16 mg/kg or more.

In certain embodiments, the antibody is administered once every two weeks (q2w) over at least eight weeks.

In certain embodiments, the antibody is administered once weekly (q1w) over at least eight weeks.

In certain embodiments, the antibody is administered intravenously.

In certain embodiments, the antibody is administered intravenously over a period of two hours.

In certain embodiments, the antibody comprises a variable heavy chain of the sequence QVQLVESGGGLVQPGGSLRLSCAASGFTFSSYYMNWVRQAPGKGLEWVSGISGDPSNTY YADSVKGRFTISRDNSKNTLYLQMNSLRAEDTAVYYCARDLPLVYTGFAYWGQGTLVTVSS (SEQ ID NO: 8) and a variable light chain of the sequence DIELTQPPSVSVAPGQTARISCSGDNLRHYYVYWYQQKPGQAPVLVIYGDSKRPS-GIPE RFSGSNSGNTATLTISGTQAEDEADYYCQTYTGGASLVFGGGTKLTVLGQ (SEQ ID NO: 9).

In certain embodiments, the antibody comprises an IgG1 Fc region.

In embodiments, the antibody is administered in combination with dexamethasone.

In embodiments, the antibody is administered in combination with dexamethasone, wherein dexamethasone is dosed at 20 mg or 40 mg once weekly (q1W).

EXAMPLES

Example 1: Patient Selection

The study was an open-label, multicentre, dose escalation (3+3 design) study to characterize the safety and preliminary efficacy of the human anti-CD38 antibody MOR03087 (MOR202), in adult subjects with relapsed/refractory multiple myeloma, as monotherapy and in adult subjects with relapsed/refractory multiple myeloma in combination with standard therapy. ClinicalTrials.gov Identifier: NCT01421186.

Patients were eligible to participate in the study if they met the following criteria:

1. were >18 years of age,
2. Relapsed or refractory multiple myeloma defined as:

Parts A, B and C:

(i) Failure of at least 2 previous therapies which must have included an immunomodulatory agent and a proteasome inhibitor (either together or part of different therapies) (ii) All subjects must have documented progression during or after their last prior therapy for multiple myeloma Part D:

(i) At least 2 previous therapies including lenalidomide and a proteasome inhibitor (ii) All subjects must have documented progression during or within 60 days after their last prior therapy for multiple myeloma Part E:

(i) Received at least one previous therapy (ii) All subjects must have documented progression during or after their last prior therapy for multiple myeloma Additional inclusion criteria were as follows:

1. Presence of serum M-protein ≥0.5 g per 100 mL (≥5 g/L) and/or urine M-protein ≥200 mg per 24-hour period 2. Absolute neutrophil count (ANC)≥1,000/mm3

3. Haemoglobin ≥8 g/dL, and

4. Ability to comply with all study related procedures, medication use and evaluations.

The main exclusion criteria were primary, refractory MM; solitary plasmacytoma or plasma cell leukemia; and previous allogenic stem cell transplant.

Tables 1A and B describes the demographics of the patients treated in the present study.

TABLE 1A

Demographics of Patients Treated in the present Study as of Apr. 13, 2015

| Cohorts | 1-4 | 5-8 | Total |
|---|---|---|---|
| Dosing (mg/kg) | 0.01-0.5 | 2-16 | |
| Patients treated | 14 | 28 | 42 |
| Median age (years) | 70 | 69.5 | 69.5 |
| Gender, % | | | |
| Female | 42.9 | 28.6 | 33.3 |
| Male | 57.1 | 71.4 | 66.7 |
| Ethnicity, % | | | |
| Caucasian | 100 | 100 | 100 |
| Median Karnofsky PS (%) | 90 | 90 | 90 |
| Median number of prior therapy lines (range) | 4 (2-10) | 4 (2-11) | 4 (2-11) |
| ASCTs (%) | 93 | 75 | 81 |
| Prior therapies, % (selection) | | | |
| Bortezomib | 100 | 100 | 100 |
| Carfilzomib | 0 | 7.1 | 4.8 |
| Thalidomide | 35.7 | 39.3 | 38.1 |
| Lenalidomide | 100 | 96.4 | 97.6 |
| Pomalidomide | 0 | 21.4 | 14.3 |
| Melphalan | 100 | 96.4 | 97.6 |
| Cyclophosphamide | 64.3 | 82.1 | 76.2 |
| Doxorubicin | 57.1 | 60.7 | 59.5 |

ASCTs Autologous Stem Cell Transplant;
PS, performance status.

TABLE 1B

Demographics of Patients Treated in the present Study as of Oct. 26, 2015

| | Schedule | | |
|---|---|---|---|
| | q1w + Dex | Q1W + POM/Dex | Q1w + LEN/Dex |
| Dosing (mg/kg) | 4-16 | 8 | 8 |
| Patients treated | 10 | 3 | 4 |
| Median age (years) | 68 | 64 | 59 |
| Gender, % | | | |
| Female | 60 | 67 | 75 |
| Male | 40 | 33 | 25 |
| Ethnicity, % | | | |
| Caucasian | 100 | 100 | 100 |
| Median Karnofsky PS (%) | 90 | 100 | 95 |
| Median number of prior therapy lines (range) | 4 | 3 | 2 |
| ASCTs (%) | 80 | 33 | 75 |
| Prior therapies, % (selection) | | | |
| Bortezomib | 100 | 100 | 100 |
| Lenalidomide | 100 | 100 | 25 |
| Cyclophosphamide | 90 | 33 | 100 |
| Melphalan | 80 | 100 | 75 |
| Doxorubicin | 60 | 0 | 50 |
| Thalidomide | 50 | 0 | 0 |
| Pomalidomide | 10 | 0 | 0 |
| Carfilzomib | 10 | 0 | 0 |
| Panobinostat | 0 | 0 | 25 |

ASCT, autologous stem cell transplant;
Dex, dexamethasone;
LEN, lenalidomide;
POM, pomalidomide;
PS, performance status; q1w, weekly.

Example 2: Study Design

The primary study outcome measures were as follows:

1. Identify the maximum tolerated dose (MTD) and/or recommended dose/schedule of MOR202 as monotherapy with and without dexamethasone (DEX), and in combination with pomalidomide (POM)/DEX and lenalidomide (LEN)/DEX.

2. Evaluate safety by the incidence and severity of adverse events (AEs).

3. Evaluate the immunogenicity of MOR202.

The Secondary outcome measures were as follows:

1. Evaluate the pharmacokinetics (PK) of MOR202 without and with POM/DEX and LEN/DEX.

2. Identify the overall response rate, duration of response, time-to-progression, and progression-free survival.

Patients were allocated to the following cohorts:

| Dose-escalation Cohorts | Part A: 2-hour IV infusion of MOR202 Cohorts 1-8: 0.01→0.04→0.15→0.5→1.5→4.0→8.0→16.0 mk/kg, without DEX, q2w | |
|---|---|---|
| | Part B: 2-hour IV infusion of MOR202 (Cohorts 6b-8b): 4→(8)→(16) mg/kg, without DEX, q1w | Part C: 2-hour IV infusion of MOR202 (Cohorts 6c-8c): 4→8→16 mg/kg, with DEX, q1w |
| | Part D: 2-hour IV infusion of MOR202 (Cohorts 7d-8d): 8→16 mg/kg, with POM/DEX, q1w | Part E: 2-hour IV infusion of MOR202 (Cohorts 7e-8e): 8→16 mg/kg, with LEN/DEX, q1w |

-continued

| | |
|---|---|
| Confirmatory Cohorts (26 patients each) | MOR202 monotherapy without/with DEX, q1w or q2w<br>MOR202 with POM/DEX, q1w<br>MOR202 with LEN/DEX, q1w | q1w: weekly;
q2w: every 2 weeks;
DEX: dexamethasone;
LEN: lenalidomide;
POM: pomalidomide.

Treatment cycles were 28 days. Initial MOR03087 doses were 0.01 mg/kg in part A, 4 mg/kg in parts B and C and 8 mg/kg in parts D and E; in all parts MOR03087 doses was escalated to a maximum of 16 mg/kg. In part A, patients received a biweekly intravenous infusion of MOR03087 which was administered on days 1 and 15 of the cycle. In parts B to E patients received a weekly intravenous infusion of MOR03087 which was administered on days 1, 8, 15, and 22 of the cycle.

In all parts a loading dose of MOR03087 was administered on day 4 of cycle 1.

Where applicable, dexamethasone was administered to patients orally; 40 mg 75 years old) or 20 mg (>75 years old) on days 1, 8, 15, and 22 of the 28-day cycle. An additional dose was administered in cycle 1 on day 4.

For the relevant cohorts, Pomalidomide was administered to patients orally 4 mg on days 1-21 of the 28-day cycle.

For the relevant cohorts, Lenalidomide was administered to patients orally 25 mg on days 1-21 of the 28-day cycle.

For all parts, patients will be treated until disease progression or until a maximum of 2 years after first treatment.

Example 3: Study Completion

Parts A-C were conducted in patients with rrMM who had failed 2 previous therapies including an immunomodulatory drug and a proteasome inhibitor.

The duration of treatment was as follows:

Patients from part A (cohorts 1-6) were treated for up to 2 cycles only (2×28 days). Patients from subsequent cohorts were/will be treated until disease progression (PD) for up to 2 years.

The route of MOR202 administration was a 2-hour intravenous (IV) infusion.

The premedication, where applicable was antipyretic, histamine H1 receptor blocker.

On completion of parts A-E, confirmatory cohorts (of patients each) are planned to validate the MTD and/or recommended dose/schedule of MOR202 as monotherapy with and without dexamethasone (q1w or q2w), and in combination with POM/DEX and LEN/DEX (q1w).

As of Apr. 13, 2015, 42 patients had been treated; 14 and 28 patients in cohorts 1-4 and 5-8, respectively.

As of 26 Oct. 2015, a total of 52 patients had been treated with 17 of these patients being treated with the clinically relevant dose regimens

Example 4: Toxicity Assessment 42 (100%) patients experienced adverse events (AEs) during treatment irrespective of causality.

18 (42.9%) patients discontinued treatment with 3 (7.1%) patients due to suspected causal relationship.

There have been no treatment-related deaths.

The Maximum Tolerated Dose (MTD) of MOR202 has not yet been reached.

Table 2 shows the most frequently reported AEs.

TABLE 2

Most frequently reported AEs as of Apr. 13, 2015

| | Cohort 1-4 | | Cohort 5-8 | | Total | |
|---|---|---|---|---|---|---|
| Hematologic AEs* (≥10%) | | | | | | |
| Anemia | 7.1 | 42.9 | — | 28.6 | 2.4 | 33.3 |
| Lymphocyte count decreased | — | 7.1 | 21.4 | 25.0 | 14.3 | 19.0 |
| WBC** count decreased | 7.1 | 7.1 | 7.1 | 25.0 | 7.1 | 19.0 |
| Leukopenia | — | 7.1 | 7.1 | 17.9 | 4.8 | 14.3 |
| Neutrophil count decreased | — | 0.0 | 3.6 | 17.9 | 2.4 | 11.9 |
| Thrombocytopenia | — | 0.0 | 7.1 | 17.9 | 4.8 | 11.9 |
| Non-hematologic AEs (≥15%) | | | | | | |
| Fatigue | — | 42.9 | — | 28.6 | — | 33.3 |
| Nausea | — | 35.7 | — | 21.4 | — | 26.2 |
| Diarrhea | — | 28.6 | — | 14.3 | — | 19.0 |
| Headache | — | 42.9 | — | 3.6 | — | 16.7 |
| Nasopharyngitis | — | 28.6 | — | 10.7 | — | 16.7 |
| Pyrexia | — | 21.4 | — | 14.3 | — | 16.7 |

*MedDRA System Organ Classes "Blood and Lymphatic System Disorders" and "Investigations" are applicable and therefore Preferred Terms from both are included;
**WBC, white blood cell.

Infusion Tolerability

A 2-hour IV infusion was feasible in all patients. Infusion-related reactions (IRRs) occurred in 13 (31%) patients receiving MOR202 without DEX, mainly during the first infusion.

Figure 6:
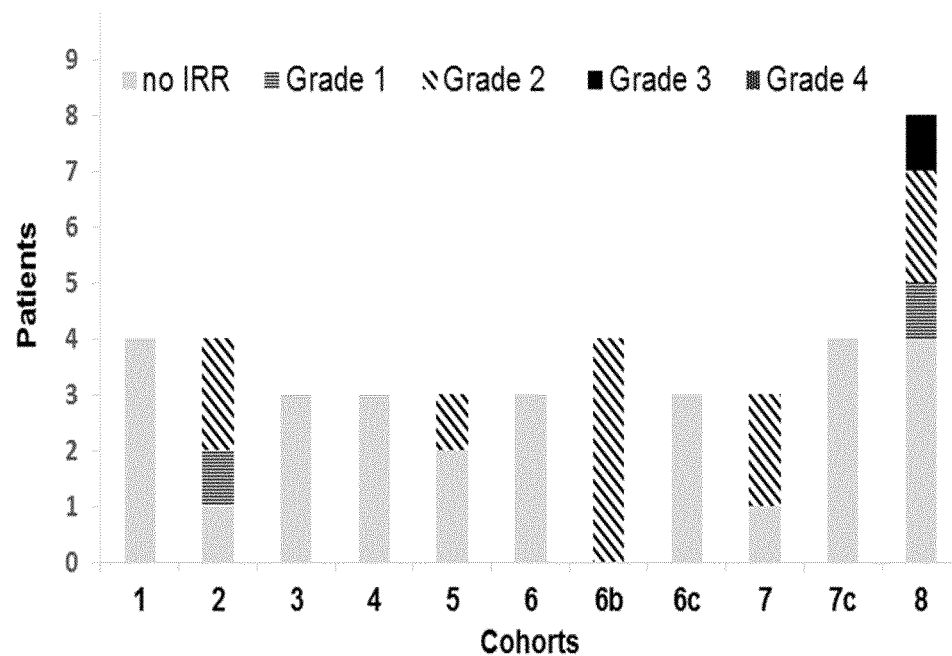
FIG. 6 shows any infusion-related reactions in the clinical trial of MOR03087 (MOR202) in adult subjects with relapsed/refractory multiple myeloma.

All IRRs were grade 1-2 except for 1 patient (grade 3). No IRRs occurred in patients who received DEX. IRRs are shown in FIG. 6.

Example 5: Treatment Administered and Response Assessment

Figure 2:
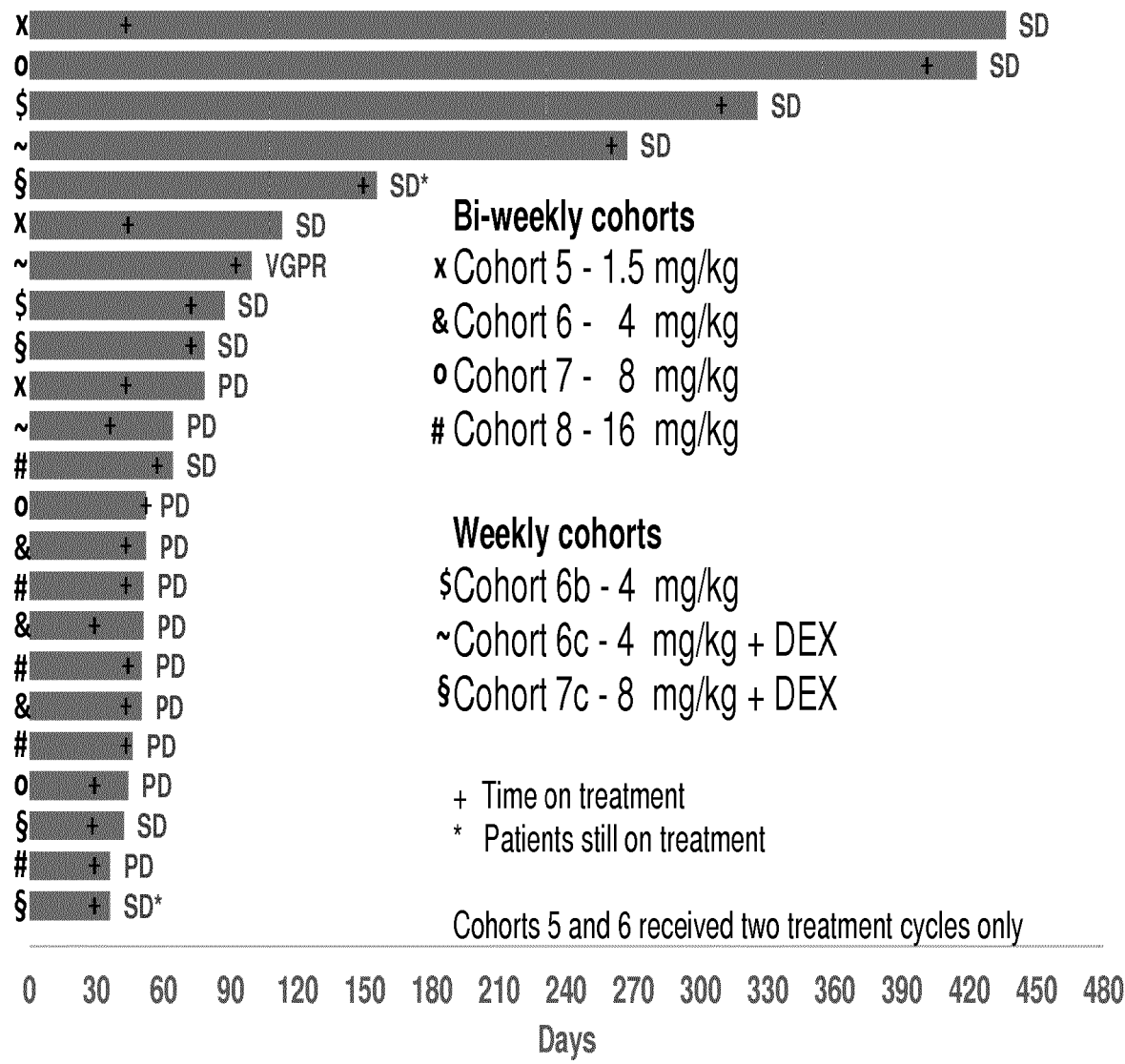
FIG. 2 shows the best responses and time on treatment for patients from cohorts 5-8 receiving at least 1 treatment cycle.
Figure 3:
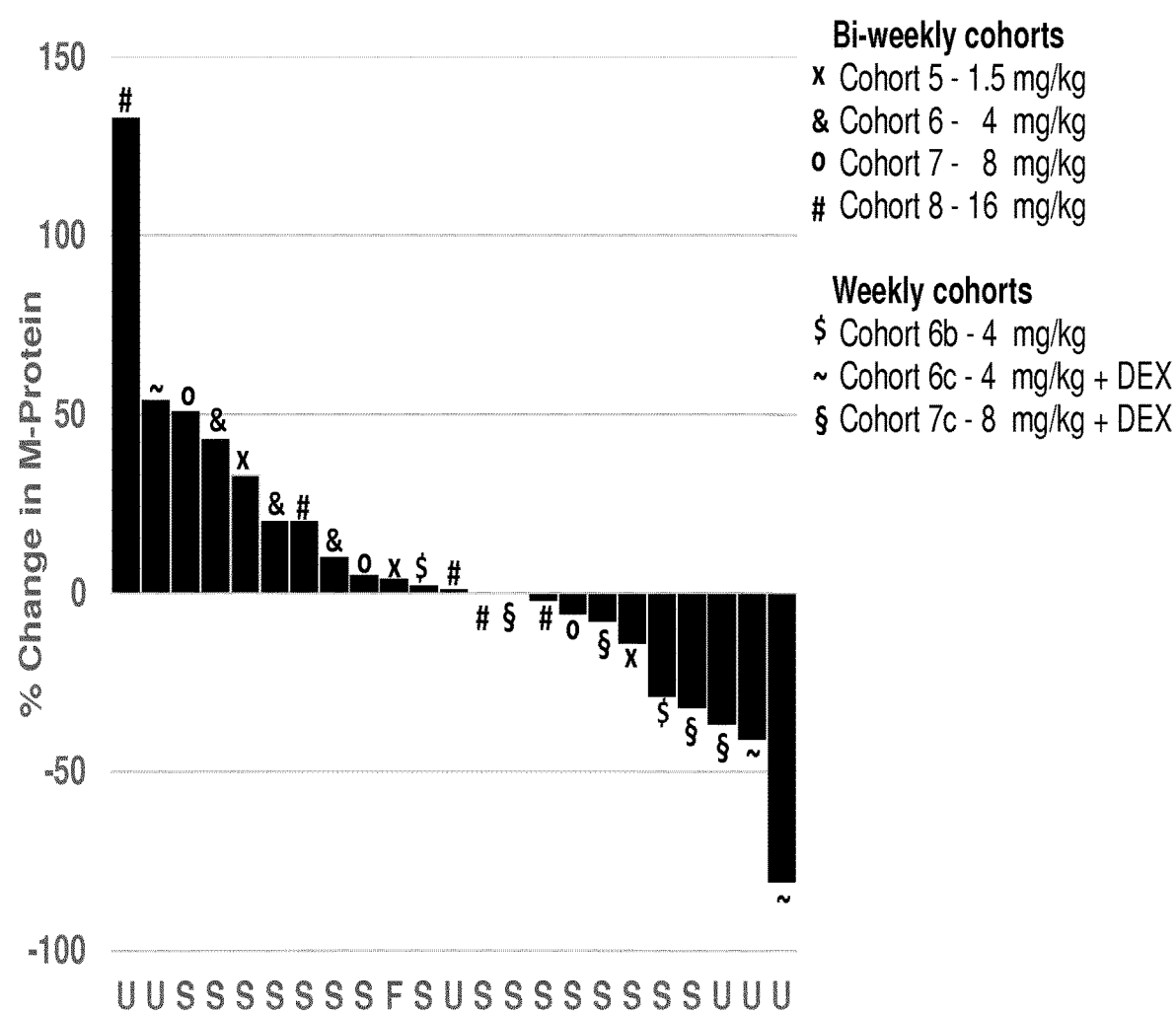
FIG. 3 shows the best change in M protein for patients from cohorts 5-8 receiving at least 1 treatment cycle.

FIG. 2 shows responses as of Apr. 13, 2015. FIG. 3 shows the change in M protein to date.

The overall response rate, duration of response, time-to-progression, and progression-free survival of all patients will be evaluated.

Example 6: Pharmacokinetics

FIGS. 7A-D show the MOR202 serum concentrations over time. In most patients treated with 4 mg/kg q2w, a dominant target-mediated sink effect was observed leading to low or no detectable serum trough levels, see FIGS. 7A and C. In contrast, patients treated with ≥4 mg/kg q1w showed constant or slightly accumulating trough levels, see FIGS. 7B and D.

The data of 8 mg/kg and 16 mg/kg q2w in FIGS. 7A and C indicate that dose-escalation leads to full target saturation at these higher dose levels.

A terminal elimination half-life of 2-3 weeks was estimated by comparing modelled serum concentrations of MOR202 (at 4 mg/kg, q1w) with measured patient data.

Only 1 patient (0.15 mg/kg q2w) developed a transient anti-MOR202 antibody response.

PK data indicate the potential for full target occupancy in the majority of pts receiving 8 and 16 mg/kg q1w.

Surprisingly it was found that the overall response rate, duration of response, time-to-progression, and/or progression-free survival of patients receiving administration of 8 mg/kg once every other week q2w and/or once weekly q1w was significantly improved over patients receiving 4 mg/kg once every other week q2w or 4 mg/kg once weekly q1w.

Surprisingly it was found that the overall response rate, duration of response, time-to-progression, and/or progression-free survival of patients receiving administration of 16 mg/kg once every other week q2w and/or once weekly q1w was significantly improved over patients receiving 4 mg/kg once every other week q2w or 4 mg/kg once weekly q1w, and/or receiving 8 mg/kg once every other week q2w or 8 mg/kg once weekly q1w.

Figure 4:
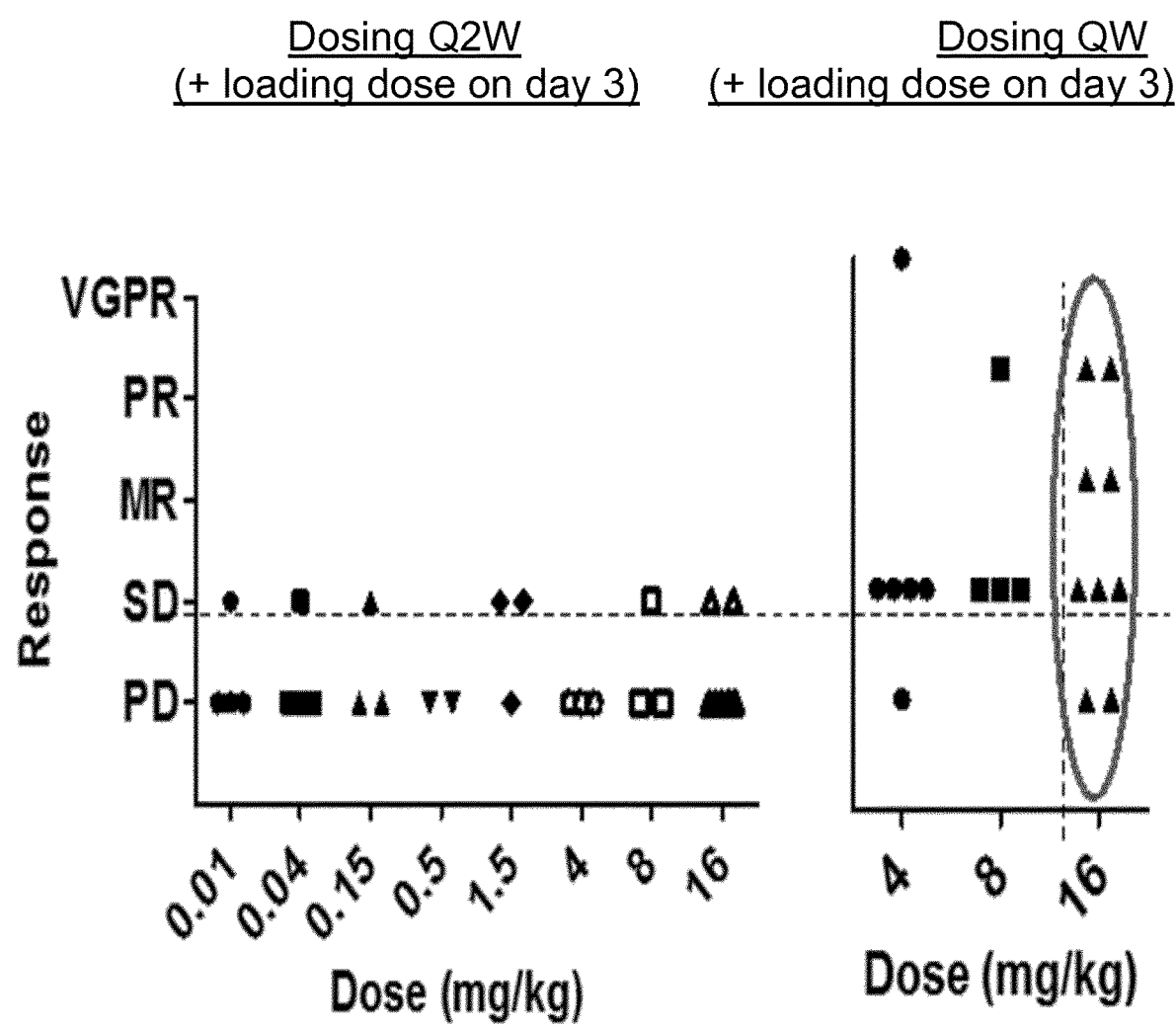
FIG. 4 shows the MOR202 dose vs. overall response results in the clinical trial of MOR03087 (MOR202) in adult subjects with relapsed/refractory multiple myeloma.
Figure 5:
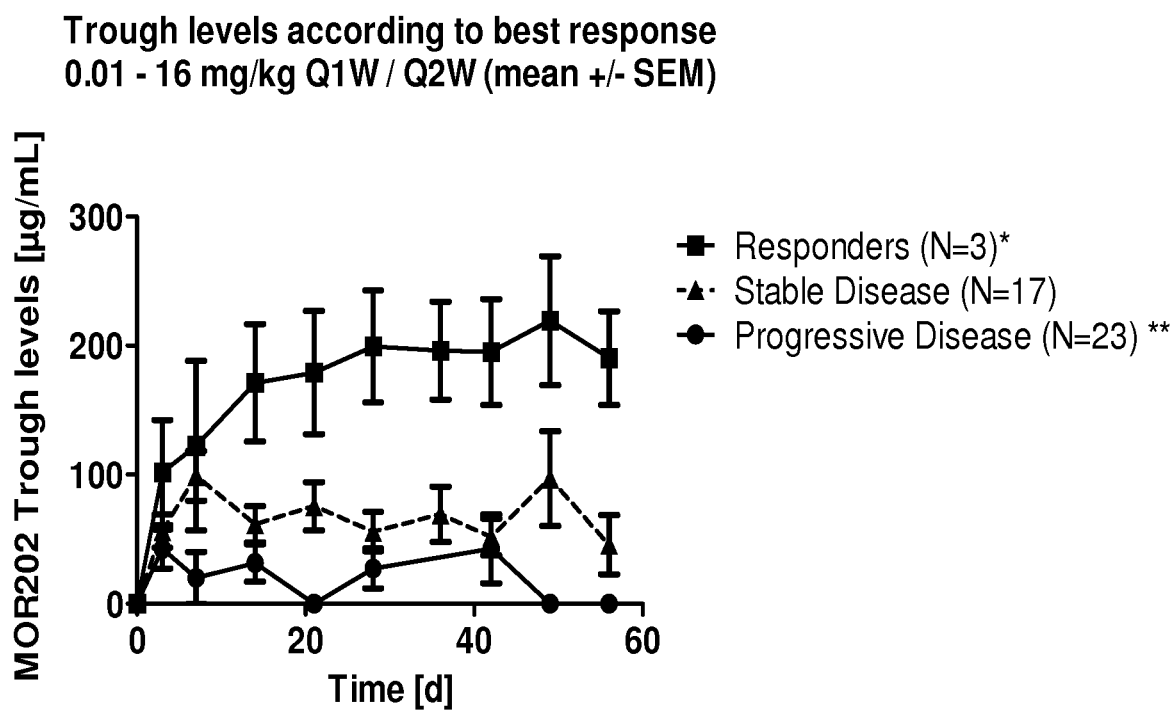
FIG. 5 shows the trough levels of MOR202 according to best response in the clinical trial of MOR03087 (MOR202) in adult subjects with relapsed/refractory multiple myeloma.

FIG. 4 shows the superior overall response rates of dosing MOR202 at 16 mg/kg once weekly q1w in the treatment of multiple myeloma. FIG. 5 supports a direct relationship between minimum trough levels of MOR202 and clinical responses, whereas higher trough levels led to better clinical responses. FIG. 8 supports the direct relationship between the MOR202 dose, frequency of dosing and trough levels showing that higher trough levels were linked to higher doses.

In summary, surprisingly it was found that the overall response rate of patients receiving administration of 16 mg/kg once weekly q1w was significantly improved over patients receiving 4 mg/kg once every other week q2w or 4 mg/kg once weekly q1w, and/or receiving 8 mg/kg once every other week q2w or 8 mg/kg once weekly q1w.

The invention claimed is:

1. A method for treatment of relapsed/refractory multiple myeloma in humans, said method comprising administering to a human patient in need an antibody specific for CD38, said antibody comprising an HCDR1 region of sequence GFTFSSYYMN (SEQ ID NO: 1) or SYYMN (SEQ ID NO: 2), an HCDR2 region of sequence GISGDPSNTYYADSVKG (SEQ ID NO: 3), an HCDR3 of sequence DLPLVYTGFAY (SEQ ID NO: 4), an LCDR1 region of sequence SGDNLRHYYVY (SEQ ID NO: 5), an LCDR2 region of sequence GDSKRPS (SEQ ID NO: 6), and an LCDR3 region of sequence QTYTGGASL (SEQ ID NO: 7), wherein said antibody is administered at a dose of 16 mg/kg or more once weekly (q1w) over at least eight weeks, wherein said antibody is administered in combination with dexamethasone dosed at 20 mg or 40 mg once weekly (q1W) to treat relapsed/refractory multiple myeloma in the human patient, wherein administration of said antibody in combination with dexamethasone significantly improves overall response of the human patient over patients receiving 4 or 8 mg/kg q1w.

2. The method according to claim 1, wherein said antibody is administered intravenously.

3. The method according to claim 1, wherein said antibody is administered intravenously over a period of two hours.

4. The method according to claim 1, wherein said antibody comprises a variable heavy chain of the sequence QVQLVESGGGLVQPGGSLRLSCAASGFTFSSYYMNWVRQAPGKGLEWVSGISGDPSNTYYADSVK GRFTISRDNSKNTLYLQMNSLRAEDTAVYYCARDLPLVYTGFAYWGQGTLVTVSS (SEQ ID NO: 8) and a variable light chain of the sequence DIELTQPPSVSVAPGQTARISCSGDNLRHYYVYWYQQKPGQAPVLVIYGDSKRPSGIPERFSGSN SGNTATLTISGTQAEDEADYYCQTYTGGASLVFGGGTKLTVLGQ (SEQ ID NO: 9).

5. The method according to claim 1, wherein said antibody comprises an IgG1 Fc region.

* * * * *

UNITED STATES PATENT AND TRADEMARK OFFICE
CERTIFICATE OF CORRECTION

PATENT NO. : 10,533,057 B2
APPLICATION NO. : 15/569495
DATED : January 14, 2020
INVENTOR(S) : Stéphane LeClair, Jan Endell and Stefan Härtle It is certified that error appears in the above-identified patent and that said Letters Patent is hereby corrected as shown below:

On the Title Page

At item (45), delete "*"

At item (*), delete "This patent is subject to a terminal disclaimer."

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Tyr Tyr Met Asn
1               5                   10

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Tyr Tyr Met Asn
1               5

<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Ile Ser Gly Asp Pro Ser Asn Thr Tyr Tyr Ala Asp Ser Val Lys
1               5                   10                  15

Gly

<210> SEQ ID NO 4
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Asp Leu Pro Leu Val Tyr Thr Gly Phe Ala Tyr
1               5                   10

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Gly Asp Asn Leu Arg His Tyr Tyr Val Tyr
1               5                   10

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Asp Ser Lys Arg Pro Ser
1               5

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Thr Tyr Thr Gly Gly Ala Ser Leu
1               5

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60
```

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 9
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg His Tyr Tyr Val
             20                  25                  30

Tyr Trp Tyr Gln Gln Lys Pro Gly Gln Ala Pro Val Leu Val Ile Tyr
         35                  40                  45

Gly Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
             85                  90                  95

Val Phe Gly Gly Gly Thr Lys Leu Thr Val Leu Gly Gln
            100                 105

<210> SEQ ID NO 10
<211> LENGTH: 300
<212> TYPE: PRT
<213> ORGANISM: Homo sapiens

<400> SEQUENCE: 10

Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val
             20                  25                  30

Leu Ile Leu Val Val Val Leu Ala Val Val Val Pro Arg Trp Arg Gln
         35                  40                  45

Gln Trp Ser Gly Pro Gly Thr Thr Lys Arg Phe Pro Glu Thr Val Leu
     50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
             85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr

```
                130              135              140
Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
        290                 295                 300

<210> SEQ ID NO 11
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
caggtgcaat tggtggaaag cggcggcggc ctggtgcaac cgggcggcag cctgcgtctg      60
agctgcgcgg cctccggatt taccttttct tcttattata tgaattgggt gcgccaagcc    120
cctgggaagg gtctcgagtg ggtgagcggt atctctggtg atcctagcaa taccatttat    180
gcggatagcg tgaaaggccg ttttaccatt tcacgtgata attcgaaaaa caccctgtat    240
ctgcaaatga acagcctgcg tgcggaagat acggccgtgt attattgcgc gcgtgatctt    300
cctcttgttt atactggttt tgcttattgg ggccaaggca ccctggtgac ggttagctca    360

<210> SEQ ID NO 12
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
gatatcgaac tgacccagcc gccttcagtg agcgttgcac caggtcagac cgcgcgtatc     60
tcgtgtagcg gcgataatct tcgtcattat tatgtttatt ggtaccagca gaaacccggg    120
caggcgccag ttcttgtgat ttatggtgat tctaagcgtc cctcaggcat cccggaacgc    180
tttagcggat ccaacagcgg caacaccgcg accctgacca ttagcggcac tcaggcggaa    240
```

```
gacgaagcgg attattattg ccagacttat actggtggtg cttctcttgt gtttggcggc    300
ggcacgaagt taaccgttct tggccag                                       327
```